United States Patent [19]

Stone

[11] Patent Number: 5,298,020
[45] Date of Patent: Mar. 29, 1994

[54] NEONATAL AUTOTRANSFUSION APPARATUS AND METHOD

[76] Inventor: Joseph J. Stone, 656 Hightree Rd., Santa Monica, Calif. 90402

[21] Appl. No.: 744,874

[22] Filed: Aug. 14, 1991

Related U.S. Application Data

[62] Division of Ser. No. 591,958, Oct. 2, 1990, Pat. No. 5,059,168.

[51] Int. Cl.⁵ ............................................. A61M 5/00
[52] U.S. Cl. ........................................ 604/53; 604/19; 604/4
[58] Field of Search .................... 604/4, 5, 6, 19, 27, 604/51, 52, 53, 319, 318, 317, 169; 128/760, 762

[56] References Cited

U.S. PATENT DOCUMENTS

| | | | |
|---|---|---|---|
| 4,447,235 | 5/1984 | Clarke | 604/169 |
| 4,865,583 | 9/1989 | Tu | 604/53 |
| 5,053,025 | 10/1991 | Knippscheer | 604/317 |
| 5,084,034 | 1/1992 | Zanotti | 604/319 |
| 5,097,842 | 3/1992 | Bonn | 128/762 |

*Primary Examiner*—Danton D. DeMille
*Assistant Examiner*—Sam Rimell
*Attorney, Agent, or Firm*—Poms, Smith, Lande & Rose

[57] ABSTRACT

Method and apparatus for collecting neonatal blood following the birth of an infant during cesarean section surgery. A needle is injected into the infant's umbilical cord and a syringe fluidly connected to the needle is aspirated to draw blood from the cord. The drawn blood is transferred to a blood storage bag in a sterile manner.

1 Claim, 1 Drawing Sheet

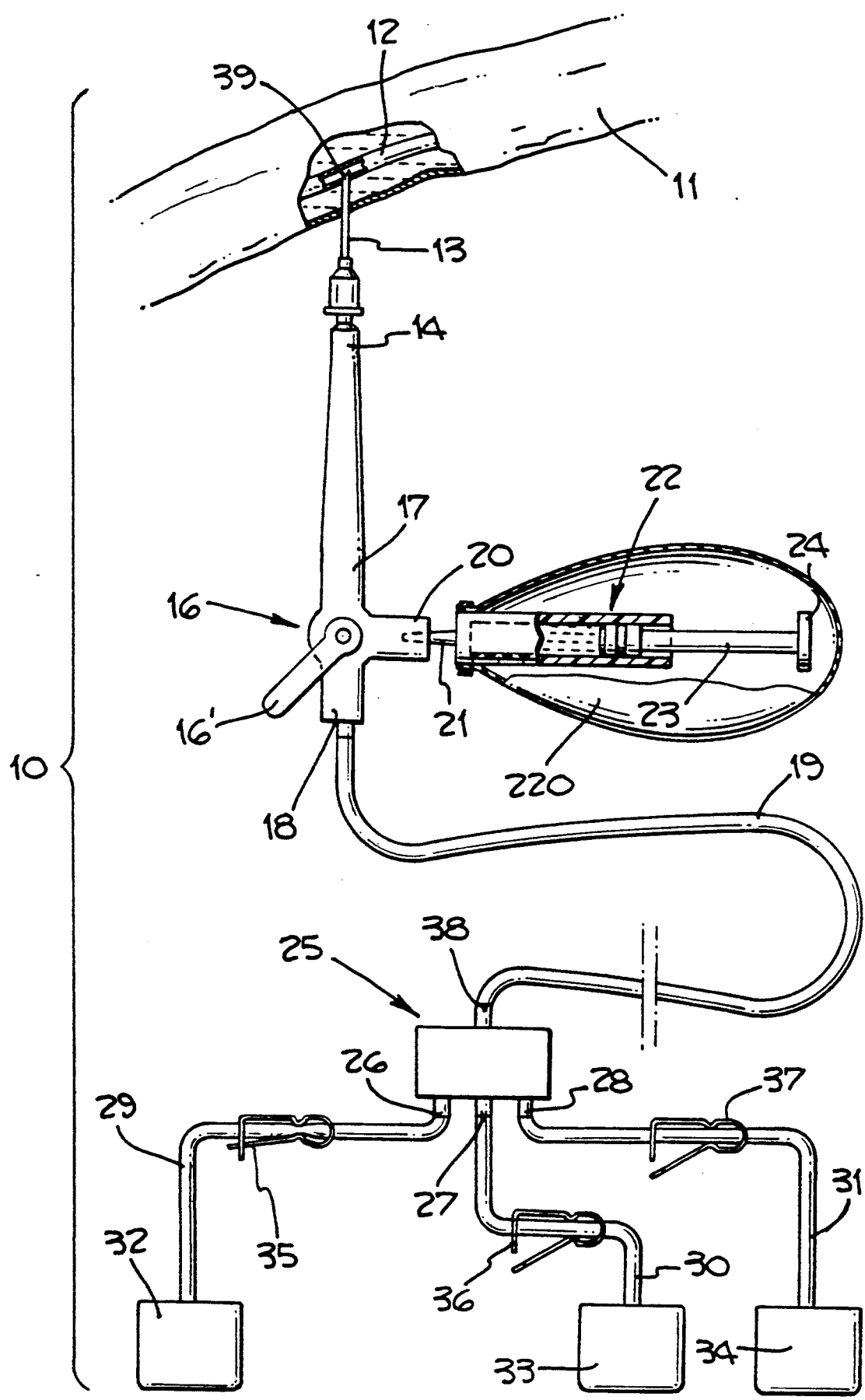

NEONATAL AUTOTRANSFUSION APPARATUS AND METHOD

This is a division of U.S. application Ser. No. 07/591,958, now U.S. Pat. No. 5,059,168.

BACKGROUND OF THE INVENTION

1. Field of the Invention

The invention relates to blood transfer devices; and, more particularly, to apparatus and method for blood transfusion to a newborn infant.

2. Description of the Prior Art

Newborn babies admitted to the intensive care unit of a hospital frequently require multiple transfusion of blood related products. Multiple donor exposures increase the risk of a child contracting hepatitis or other infectious diseases. Blood for transfusions to newborns are frequently provided by family, friends, or from the community blood bank. An autologous transfusion (the transfusion of blood from an individual to his or her self) is commonly practiced for elective surgery. However, technology does not exist at the present time to enable a newborn child to donate blood for him or herself.

Following the birth of a child during cesarean section surgery, the placenta and umbilical cord are discarded. The latter contains between 30 and 50 CC's of neonatal blood. Presently, there is no technology which allows the physician to collect blood from the umbilical cord and placenta for autologous transfusion purposes.

There is thus a need for apparatus and a method for collecting neonatal blood immediately following the birth of an infant during cesarean section surgery.

SUMMARY OF THE INVENTION

It is an object of the invention to provide apparatus and method for collecting neonatal blood following the birth of an infant during cesarean section surgery.

It is a further object of this invention to carry out the foregoing object in a quick, easy and sterile manner.

These and other objects are preferably accomplished by providing a needle which is injected into the infant's umbilical cord and a syringe fluidly connected to the needle which is aspirated to draw blood from the cord. The drawn blood is transferred to a blood storage bag in a sterile manner. A plurality of such bags may be provided, all coupled by a sterile coupler.

BRIEF DESCRIPTION OF THE DRAWING

The drawing is a schematic illustration of apparatus in accordance with the teachings of the invention.

DESCRIPTION OF THE PREFERRED EMBODIMENT

Referring now to the drawing, neonatal transfusion apparatus 10 is shown used in conjunction with the umbilical cord 11 of a newborn infant. Following the birth of an infant during cesarean surgery, the placenta (not shown) and cord 11 are normally discarded. However, such umbilical cords, as cord 11, contain between 30 and 50 ccs of neonatal blood in the umbilical vein 12. Thus, apparatus 10 includes a hollow needle 13 directly coupled via coupler 14 to a conventional stop cock 16 having an inlet 17 fluidly coupled to coupler 14. Outlet 18 is fluidly coupled to hollow flexible tubing 19 and a second outlet 20 is fluidly connected directly to a syringe 22. A plunger 23 having a handle 24 is reciprocal within syringe 22 as is well known in the art. Syringe 22 may have an internal capacity of about 20 ccs. A handle 16' is provided on stop cock 16 for selectively closing off outlet 18 or closing off inlet 17, as will be discussed. A flexible transparent plastic bag 220 may be sterilely affixed to encase syringe 22 to capture any blood leading out of the syringe 22 and its connection to outlet 20.

Tubing 19 extends to and is fluidly coupled to the inlet 38 of a coupler 25 having three outlets 26-28 fluidly coupled to tubings 29-31, respectively. Each tubing 29-31 is coupled to a conventional blood storage bag, such as bags 32 to 34, respectively. A conventional shut off clamp, such as clamps 35 to 37, is provided in each tubing 29 to 31. Bags 32-24 may have an internal capacity of about 20 cc.

The foregoing describes conventional equipment which can be quickly and easily assembled to form the apparatus of the drawing. All of the components are of course sterile.

In operation, the point 39 of needle 13 is inserted through cord 11 and into fluid communication with the umbilical vein 12 therein. Lever 16' is actuated to shut off flow through outlet 18. The plunger 23 of syringe 22 is aspirated to draw blood out of vein 12, through needle 13, into stop cock 16 through inlet 17 and into syringe 22. This draws blood out of the umbilical vein 12 into syringe 22. The doctor or surgeon can hold needle 13, stopcock 16, and aspirate syringe 22. Lever 16' is now moved to open outlet 18 and close inlet 17. One of the clamps, such as pinch clamp 35, is now squeezed open while the plunger 23 of syringe 22 is pushed inwardly. This moves blood out of syringe 22, through outlet 18 and tubing 19, into inlet 38 of device 25, and into bag 32 via tubing 29. When bag 32 is filled, clamp 35 is closed and clamp 36 is squeezed to open the same. In this manner, bags 32 to 34 can be filled with blood which blood can then be used for neonatal transfusion purposes.

The foregoing describes apparatus and method where preexisting equipment can be assembled in a manner while allowing the collecting of neonatal blood immediately following the birth of an infant during cesarean section surgery. The apparatus and method disclosed herein allows the collection of one to three aliquots of blood in bags 32 to 34 for neonatal transfusion purposes. This significantly reduces donor exposures to the newborn infant thus reducing the risk of the newborn infant contracting hepatitis or other infectious diseases.

I claim:

1. A method for collecting neonatal blood from the umbilical cord of a newborn infant comprising the steps of:
    coupling a hollow needle having a sharp end for piercing said cord to a syringe;
    sealing said syringe within a flexible bag to seal said syringe off from the atmosphere;
    piercing said cord with the end of said needle until said end enters the interior of said cord and into the umbilical vein in said cord;
    aspirating said syringe to draw blood out of said vein and into said syringe;
    shutting off fluid flow from said needle through said syringe; and
    transferring blood from said syringe into said bag.

* * * * *